(12) United States Patent
Giles et al.

(10) Patent No.: US 9,408,939 B2
(45) Date of Patent: Aug. 9, 2016

(54) ANTI-MICROBIAL AIR PROCESSOR FOR A PERSONAL PATIENT WARMING APPARATUS

(71) Applicant: Medline Industries, Inc., Mundelein, IL (US)

(72) Inventors: Andrew Giles, Libertyville, IL (US); Peter Nichol, Grayslake, IL (US)

(73) Assignee: Medline Industries, Inc., Mundelein, IL (US)

( * ) Notice: Subject to any disclaimer, the term of this patent is extended or adjusted under 35 U.S.C. 154(b) by 279 days.

(21) Appl. No.: 13/832,514

(22) Filed: Mar. 15, 2013

(65) Prior Publication Data

US 2014/0271374 A1    Sep. 18, 2014

(51) Int. Cl.
*A61L 9/20* (2006.01)
*A61L 9/22* (2006.01)
*F24F 3/16* (2006.01)

(52) U.S. Cl.
CPC .... *A61L 9/22* (2013.01); *A61L 9/20* (2013.01); *F24F 2003/1664* (2013.01); *F24F 2003/1682* (2013.01)

(58) Field of Classification Search
CPC .................................. A61L 9/20; A61L 9/22
See application file for complete search history.

(56) References Cited

U.S. PATENT DOCUMENTS

| | | | |
|---|---|---|---|
| 2,255,376 A | 9/1941 | Bull et al. | |
| 2,441,005 A | 5/1948 | Bradford | |
| 2,473,183 A | 6/1949 | Watson | |
| 2,630,288 A | 3/1953 | Eubanks, Sr. | |
| 2,688,070 A | 8/1954 | Freedlander | |
| 3,013,141 A | 12/1961 | Ellis | |
| 3,349,359 A | 10/1967 | Morey | |
| 3,423,574 A | 1/1969 | Shomphe et al. | |
| 3,480,760 A | 11/1969 | Young | |
| 3,553,749 A | 1/1971 | Majeske | |
| 3,889,101 A | 6/1975 | Woods | |

(Continued)

FOREIGN PATENT DOCUMENTS

| | | |
|---|---|---|
| CA | 969621 | 6/1975 |
| CN | 2135776 | 6/1993 |

(Continued)

OTHER PUBLICATIONS

"Snorkels". Internet Archive Wayback Machine capture from Mar. 7, 2012.*

(Continued)

*Primary Examiner* — Sean E Conley
*Assistant Examiner* — Donald Spamer
(74) *Attorney, Agent, or Firm* — Fitch, Even, Tabin & Flannery LLP

(57) ABSTRACT

An anti-microbial air processor is configured and arranged to fit at least substantially across an airway in a personal patient-warming apparatus to thereby inactivate airborne microbes before those airborne microbes are exposed to a patient via warming air delivered by the personal patient-warming apparatus. By one approach, the anti-microbial air processor comprises an anti-microbial air filter. By another approach, in lieu of the foregoing or in combination therewith, the anti-microbial air processor comprises one or more ultraviolet light sources configured to expose at least one inner surface of the personal patient-warming apparatus to ultraviolet light to thereby inactivate microbes.

17 Claims, 2 Drawing Sheets

(56) References Cited

U.S. PATENT DOCUMENTS

| | | |
|---|---|---|
| 3,898,427 A | 8/1975 | Levin |
| 3,900,654 A | 8/1975 | Stinger |
| 3,924,284 A | 12/1975 | Nelson |
| 4,047,254 A | 9/1977 | Hamasu |
| 4,108,146 A | 8/1978 | Golden |
| 4,162,393 A | 7/1979 | Balboni |
| 4,204,612 A | 5/1980 | Schrader et al. |
| 4,310,745 A | 1/1982 | Bender |
| 4,388,738 A | 6/1983 | Wagner |
| 4,423,308 A | 12/1983 | Callaway et al. |
| 4,607,624 A | 8/1986 | Jefferson |
| 4,633,062 A | 12/1986 | Nishida |
| 4,669,468 A | 6/1987 | Cartmell |
| 4,672,176 A | 6/1987 | Kishimoto et al. |
| 4,788,417 A | 11/1988 | Graflind |
| 4,825,868 A | 5/1989 | Susa et al. |
| 4,833,305 A | 5/1989 | Mashimo et al. |
| 5,031,261 A | 7/1991 | Fenner, Sr. |
| 5,081,339 A | 1/1992 | Stine |
| 5,136,741 A | 8/1992 | Balonick et al. |
| 5,138,138 A | 8/1992 | Theilacker et al. |
| 5,141,006 A * | 8/1992 | Lee et al. ............. 131/331 |
| 5,228,974 A | 7/1993 | Kiesele et al. |
| 5,240,478 A | 8/1993 | Messina |
| 5,251,347 A | 10/1993 | Hopper |
| 5,265,296 A | 11/1993 | Abbas et al. |
| 5,284,701 A | 2/1994 | Hamon |
| 5,300,098 A | 4/1994 | Philipot |
| 5,324,911 A | 6/1994 | Cranston et al. |
| 5,371,340 A | 12/1994 | Stanfield |
| 5,381,510 A | 1/1995 | Ford et al. |
| 5,385,529 A | 1/1995 | Koch |
| 5,398,354 A | 3/1995 | Balonick et al. |
| 5,451,747 A | 9/1995 | Sullivan et al. |
| 5,494,051 A | 2/1996 | Schneider, Sr. |
| 5,516,189 A | 5/1996 | Ligeras |
| 5,533,305 A | 7/1996 | Bielecki |
| 5,604,021 A | 2/1997 | Wagner |
| 5,623,760 A | 4/1997 | Newham |
| 5,720,774 A | 2/1998 | Glucksman |
| 5,729,653 A | 3/1998 | Magliochetti |
| 5,785,716 A | 7/1998 | Bayron et al. |
| 5,807,332 A | 9/1998 | Augustine et al. |
| 5,808,540 A | 9/1998 | Wheeler et al. |
| 5,817,146 A | 10/1998 | Augustine |
| 5,875,282 A | 2/1999 | Jordan et al. |
| 5,876,489 A * | 3/1999 | Kunisaki et al. ............. 96/226 |
| 5,881,410 A | 3/1999 | Yamada |
| 5,932,129 A | 8/1999 | Hyatt |
| 5,948,303 A | 9/1999 | Larson |
| 6,006,136 A | 12/1999 | Glucksman |
| 6,025,782 A | 2/2000 | Newham |
| 6,050,265 A | 4/2000 | Richardson |
| 6,142,974 A | 11/2000 | Kistner et al. |
| 6,297,738 B1 | 10/2001 | Newham |
| 6,307,168 B1 | 10/2001 | Newham |
| 6,351,678 B1 | 2/2002 | Borders |
| 6,369,369 B2 | 4/2002 | Kochman et al. |
| 6,392,209 B1 | 5/2002 | Oppitz |
| 6,464,666 B1 | 10/2002 | Augustine et al. |
| 6,497,951 B1 | 12/2002 | DeAngelis et al. |
| 6,545,253 B2 | 4/2003 | Lin et al. |
| 6,582,456 B1 | 6/2003 | Hand et al. |
| 6,596,018 B2 | 7/2003 | Endo et al. |
| 6,611,659 B2 | 8/2003 | Meisiek |
| 6,653,607 B2 | 11/2003 | Ellis et al. |
| 6,658,994 B1 | 12/2003 | McMillan |
| 6,906,293 B2 | 6/2005 | Schmiz et al. |
| 6,924,467 B2 | 8/2005 | Ellis et al. |
| 6,933,469 B2 | 8/2005 | Ellis et al. |
| 6,967,309 B2 | 11/2005 | Wyatt et al. |
| 7,010,221 B2 | 3/2006 | Augustine et al. |
| 7,079,036 B2 | 7/2006 | Cooper et al. |
| 7,094,219 B2 | 8/2006 | Noice et al. |
| 7,135,036 B2 | 11/2006 | Yue |
| 7,176,419 B2 | 2/2007 | Ellis et al. |
| 7,196,289 B2 | 3/2007 | Ellis et al. |
| 7,319,207 B2 | 1/2008 | Campf et al. |
| 2001/0020303 A1 | 9/2001 | Endo et al. |
| 2001/0022804 A1 | 9/2001 | Helmig et al. |
| 2001/0029367 A1 | 10/2001 | Fleenor |
| 2002/0019654 A1 | 2/2002 | Ellis et al. |
| 2002/0072288 A1* | 6/2002 | Hei et al. ............. 442/59 |
| 2002/0117495 A1 | 8/2002 | Kochman et al. |
| 2002/0133213 A1 | 9/2002 | Tippitt |
| 2002/0156509 A1 | 10/2002 | Cheung |
| 2003/0006229 A1 | 1/2003 | Lin et al. |
| 2003/0013998 A1 | 1/2003 | Augustine |
| 2003/0178414 A1 | 9/2003 | DeAngelis et al. |
| 2003/0218003 A1 | 11/2003 | Ellis et al. |
| 2004/0003611 A1 | 1/2004 | Walter |
| 2004/0149711 A1 | 8/2004 | Wyatt |
| 2004/0172108 A1 | 9/2004 | Cochenour et al. |
| 2005/0221037 A1 | 10/2005 | Panyard |
| 2006/0052852 A1 | 3/2006 | Wyatt |
| 2006/0162074 A1 | 7/2006 | Bader |
| 2006/0195168 A1 | 8/2006 | Dunbar |
| 2007/0010860 A1 | 1/2007 | Gafni |
| 2007/0016271 A1 | 1/2007 | Hammond |
| 2007/0036696 A1* | 2/2007 | McEllen et al. ............. 422/186.3 |
| 2007/0194913 A1 | 8/2007 | Yokoshima |
| 2008/0119757 A1 | 5/2008 | Winter |
| 2008/0249521 A1 | 10/2008 | Dunning |
| 2008/0255641 A1 | 10/2008 | Ellis |
| 2008/0269186 A1* | 10/2008 | Bignozzi et al. ............. 514/185 |
| 2010/0185195 A1 | 7/2010 | McPherson |
| 2010/0217260 A1 | 8/2010 | Aramayo |
| 2012/0024833 A1 | 2/2012 | Klewer |
| 2012/0279953 A1 | 11/2012 | Augustine |
| 2013/0060308 A1 | 3/2013 | Ellis |
| 2013/0237983 A1 | 9/2013 | Giles |

FOREIGN PATENT DOCUMENTS

| | | |
|---|---|---|
| CN | 2200983 Y | 6/1995 |
| CN | 1469992 | 1/2004 |
| CN | 2781925 Y | 5/2006 |
| DE | 2308214 | 8/1974 |
| DE | 3146234 | 5/1983 |
| DE | 3405425 | 8/1985 |
| DE | 3707948 | 9/1988 |
| DE | 29809445 | 8/1998 |
| EP | 677283 | 10/1995 |
| EP | 0757907 | 2/1997 |
| GB | 2255262 | 10/1992 |
| JP | 57180888 | 11/1982 |
| JP | 6318117 | 2/1988 |
| JP | 2276185 | 11/1990 |
| JP | 3165746 | 7/1991 |
| JP | 473883 | 3/1992 |
| JP | 4073883 | 3/1992 |
| JP | 1043258 | 2/1998 |
| JP | 11214131 | 8/1999 |
| JP | 2001238924 | 9/2001 |
| JP | 2001327551 | 11/2001 |
| KR | 10005008420 | 1/2005 |
| WO | WO0195841 | 12/2001 |
| WO | 03072188 | 9/2003 |
| WO | WO2006076148 | 7/2006 |
| WO | WO2006086513 | 8/2006 |
| WO | WO2008110922 | 9/2008 |
| WO | 2008122043 | 10/2008 |
| WO | 2012122002 | 9/2012 |
| WO | 2013134477 | 9/2013 |

OTHER PUBLICATIONS

Albrecht et al.; Forced-Air Warming Blowers: An Evaluation of Filtration Adequacy and Airborne Contamination Emissions in the Operating Room; Association for Professionals in Infection Control and Epidemiology, Inc., Published by Elsevier Inc., Copyright 2011.
Australian Patent Application No. 2008224637; Patent Examination Report No. 1; Dated: Jul. 13, 2012.

(56) References Cited

OTHER PUBLICATIONS

Chinese Patent Application No. 200880007958.6; English Translation of Third Office Action; Dated: Sep. 12, 2012.
Chinese Patent Application No. 200880007958.6; Fourth Office Action Dated Feb. 22, 2013.
Chinese Patent Application No. 20088007958.6; First Office Action with English Translation; Dated: Apr. 6, 2011.
Chinese Patent Application No. 20088007958.6; Second Office Action with English Translation; Dated: Nov. 23, 2011.
*Medline Industries, Inc.* v. *Augustine Temperature Management LLC and Augustine Biomedical Design LLC*; Civil Action No. 1:12-cv-1620; Defendants' Answer and Affirmative Defenses, Defendants' Denial of Personal Jurisdiction as to Augustine Biomedical and Design, LLC, and Defendant, Augustine Temperature Management LLC's Counterclaims; Dated: May 22, 2012.
*Medline Industries, Inc.* v. *Augustine Temperature Management LLC and Augustine Biomedical Design LLC*; Civil Action No. 1:12-cv-1620; Defendants' Initial Infringement and Invalidity Contentions; Dated: Jul. 3, 2012.
PCT Patent Application No. PCT/IB2008/000771; International Search Report Dated Aug. 27, 2008.
PCT Patent Application No. PCT/IB2008/000771; Written Opinion Dated Sep. 15, 2009.
PCT Patent Application No. PCT/US01/18927; International Preliminary Examination Report Dated Jun. 20, 2003.
PCT Patent Application No. PCT/US01/18927; International Preliminary Examination Report Dated May 22, 2003.
PCT Patent Application No. PCT/US01/18927; International Search Report Dated Feb. 12, 2004.
PCT Patent Application No. PCT/US01/18927; International Search Report Dated Jan. 7, 2004.
PCT Patent Application No. PCT/US01/18927; International Search Report Dated May 7, 2002.
PCT Patent Application No. PCT/US01/18927; Partial International Search Dated Dec. 21, 2001.
PCT Patent Application No. PCT/US03/12168; International Search Report Dated Jan. 7, 2004.
PCT Patent Application No. PCT/US03/28458; International Search Report Dated Feb. 12, 2004.
PD McGovern et al.; Forced Air Warming and Ultra-Clean Ventilation Do Not Mix; Northumbria Healthcare NHS Foundation Trust; vol. 93-B, No. 11, Nov. 2011.
Stretch Conductive Fabric; Less EMF Inc.; at least as of Mar. 6, 2002.
International Search Report and The Written Opinion of the International Searching Authority from PCT/US2014/023560 Dated Jun. 25, 2014.
International Search Report and Written Opinion of the International Searching Authority for PCT/US2014/023641 dated Jun. 24, 2014.
Written Opinion Dated Oct. 1, 2002 from PCT Patent Application No. PCT/US01/18927.
International Search Report Dated Jun. 12, 2013; from PCT Patent Application No. PCT/US2013/029540.
*Medline Industries, Inc.* v. *Augustine Temperature Management LLC and Augustine Biomedical Design, LLC*; Case No. 1:12-cv-1620; Defendants' Initial Non-Infringement and Invalidity Contentions; Dated: Jul. 3, 2012.
PCT Patent Application No. PCT/IB2008/000771; International Preliminary Report on Patentability and Written Opinion Dated Sep. 15, 2009.
PCT Patent Application No. PCT/IB2008/000771; Written Opinion of the International Searching Authority; Dated: Aug. 27, 2008.
PCT Patent Application No. PCT/US01/18927; International Preliminary Search Report Dated May 22, 2003.
International Search Report and The Written Opinion of the International Searching Authority from PCT/US2014/023344 dated Jun. 3, 2014.

\* cited by examiner

ANTI-MICROBIAL AIR PROCESSOR FOR A PERSONAL PATIENT WARMING APPARATUS

TECHNICAL FIELD

This invention relates generally to personal patient warmers.

BACKGROUND

Personal patient warming apparatuses are known in the art. Being "personal," these apparatuses do not serve in any meaningful way to warm a general area (such as a room). Instead, these apparatuses serve to provide local-to-a-patient warming for the benefit of an individual patient (typically during the administration of a medical-services procedure such as but not limited to an operation). While some of the delivered warmth will typically escape beyond the patient themselves, the focus of the warmth delivery mechanism is intended and designed to primarily warm the patient as versus the local environment.

One category of personal patient warming apparatuses serves to deliver warmed air to the patient. By one common approach, the personal patient warming apparatus includes a blanket that overlies the patient. This blanket includes one or more internal pneumatic chambers. A blower forces warmed air into the blanket and that warmed air then exits the blanket via a plurality of small orifices (typically located on an underside surface of the blanket). The exiting warmed air, in turn, provides local warming in very close proximity to the patient.

While such an approach can serve very well to warm a patient in a highly localized and controlled manner, there is the potential for such an approach to introduce new complications as well. For example, the warmed air directed to the patient may include potentially harmful microbes. The sources of such microbes are many and varied. Some operating rooms, for example, use a top-to-bottom air flow ventilation system. In such a case the most contaminated air in the room will typically be near the floor. Unfortunately, the air-intake for the heater/blower of the personal patient warming apparatus may also be located near the floor, hence encouraging the intake of contaminated air. In other cases, and as another example, the microbes may be growing with the pneumatic pathways of the heater/blower itself.

Many personal patient warming apparatuses include a particulate filter (not to be confused with a HEPA filter). While suitable to block larger particles such as certain dust particles, such a filter will not ordinarily block the passage of microbes. Accordingly, if potentially-harmful microbes are present, the usual filters employed in available personal patient warming apparatuses are largely ineffectual to keep those microbes separated from the patient. Exposure to microbes, in turn, carries with it a risk of infection and attending complications.

BRIEF DESCRIPTION OF THE DRAWINGS

The above needs are at least partially met through provision of the an anti-microbial air processor for a personal patient-warming apparatus described in the following detailed description, particularly when studied in conjunction with the drawings, wherein.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments an anti-microbial air processor is configured and arranged to fit at least substantially across an airway in a personal patient-warming apparatus to thereby inactivate airborne microbes before those airborne microbes are exposed to a patient via warming air delivered by the personal patient-warming apparatus. By one approach, the anti-microbial air processor comprises an anti-microbial air filter. By another approach, in lieu of the foregoing or in combination therewith, the anti-microbial air processor comprises one or more ultraviolet light sources configured to expose at least one inner surface of the personal patient-warming apparatus to ultraviolet light to thereby inactivate microbes.

These teachings are highly flexible in practice and will accommodate a wide variety of modifications and adaptations. The anti-microbial air processor can be located, for example, at any one or more of a variety of locations including but not limited to the intake for the heater/blower, the outtake for the heater/blower, within a warm air delivery tube as comprises an external part of the personal patient-warming apparatus, or even as a part of the pneumatic warming blanket that serves to ultimately bath the patient in the expelled warmed air.

So configured, such an anti-microbial air processor can contribute to at least a significant reduction in the number of active microbes that reach the patient via warmed air. The present teachings can be economically deployed and can also (at least in many cases) be applied retroactively for use with already-fielded personal patient warming apparatuses.

Figure 1:
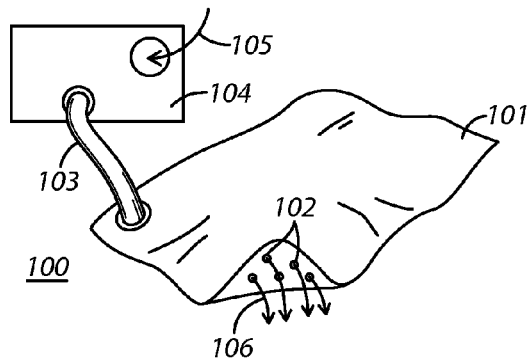
FIG. 1 comprises a schematic view as configured in accordance with the prior art.

These and other benefits may become clearer upon making a thorough review and study of the following detailed description. Referring now to the drawings, and in particular to FIG. 1, it may be helpful to first briefly recount a simple illustrative example of a personal patient warming apparatus 100 that delivers warmed air to a patient. In this example, the personal patient warming apparatus 100 includes a pneumatic blanket 101 having one or more pneumatic chambers formed therein and a plurality of small orifices 102 formed through the blanket material by which warmed air can escape from the aforementioned chamber(s).

A warm air delivery tube 103 couples the blanket's pneumatic chamber(s) to a heater/blower 104. The heater/blower 104 pulls in ambient air 105 through one or more intake ports using one or more fans or other air-moving mechanisms, warms that air using a heating methodology of choice, and pushes that warmed air out to the blanket 101 via the warm air delivery tube 103. That warmed air 106 then eventually exits the blanket 101 via the aforementioned orifices 102. When the blanket 101 overlies a patient that exiting warmed air 106 serves to provide localized warming for the patient.

Those skilled in the art will recognize that the prior art accommodates a wide number of variations as regards the foregoing. The specific construction and form factor of the blanket 101, for example, can vary considerably from one embodiment to another. As another example, there are all manner of approaches to heating the air and causing the air to move that are available for consideration. As the present teachings are not particularly sensitive to any particular selections in these regards, however, for the sake of brevity further elaboration in these regards will not be provided here aside from noting that the expression "personal patient warming apparatus" as used herein will be understood to include both the embodiment illustrated in FIG. 1 and other such variations as are reasonably associated therewith.

Figure 2:
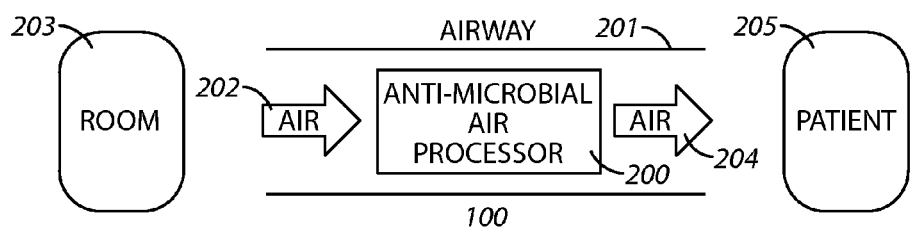
FIG. 2 comprises a side elevational schematic view as configured in accordance with various embodiments of the invention.

Referring now to FIG. 2, the present teachings provide for fitting at least one anti-microbial air processor 200 across an airway 201 of a personal patient warming apparatus 100. In particular, by one approach the anti-microbial air processor 200 is configured and arranged to fit at least substantially across the airway 201 of choice. So located, the anti-microbial air processor 200 receives incoming (upstream) air 202 (as drawn, for example, from a room 203 that contains the patient 205) and passes air 204 downstream to the patient 205.

Being an "anti-microbial" air processor 200, this air processor may or may not impede the flow of particles of one size or another but does in any event serve the purpose of inactivating at least a substantial number of microbes as pass therethrough. For example, by one approach such an anti-microbial air processor 200 may inactivate at least fifty percent of all microbes that pass therethrough. By another approach such an anti-microbial air processor 200 may inactivate at least seventy-five percent of all microbes that pass therethrough. And by yet another approach such an anti-microbial air processor 200 may inactivate at least ninety percent of all microbes that pass therethrough.

Figure 3:
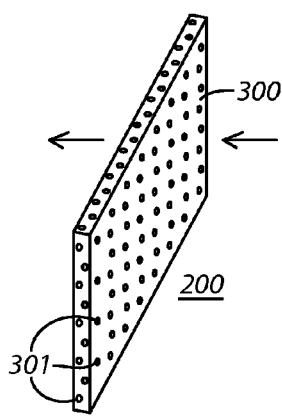
FIG. 3 comprises a perspective view as configured in accordance with various embodiments of the invention.

These teachings will accommodate a variety of different anti-microbial air processors 200. With reference to FIG. 3, by one approach the anti-microbial air processor 200 can comprise, at least in part, an anti-microbial air filter. This anti-microbial air filter can comprise, for example, at least one active layer of filter material 300. This active layer of filter material 300 can itself comprise, by one approach, a fabric substrate having a plurality of positively-charged ions 301 disposed therein. By one approach, and as an illustrative example, the fabric substrate could comprise a splunlace fabric from cellulosic (such as Rayon) fibers.

These positively-charged ions 301 can comprise, for example, copper ions, zinc ions, or silver ions, to note but a few examples in these regards, either alone or in any of a variety of combinations with one another. For example, by one approach the filter material 300 can comprise a fabric substrate having both copper ions and zinc ions disposed therein. When using a combination of ions the ratio of one type of ion to the other can vary as desired. By one approach, for example, there can be a more-or-less equal amount of copper ions as compared to zinc ions.

Such ions are positively-charged ions. In the described application setting these positively-charged ions will bind with negatively-charged groups that are present on at least some microbes. When this binding occurs the corresponding microbe is inactivated (that is, the microbe's biological ability to function in a harmful way on or in a human host is disabled).

Figure 4:
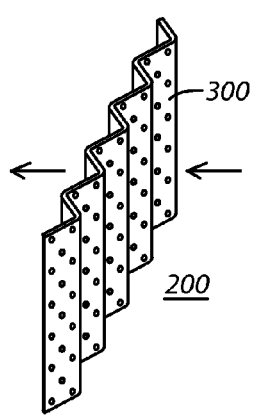
FIG. 4 comprises a perspective view as configured in accordance with various embodiments of the invention.

In the illustrative example of FIG. 3 the filter material 300 comprises a block of the desired material. If desired, and as illustrated in FIG. 4, the fabric substrate that comprises the filter material 300 can be pleated (as densely or as loosely packed as desired) to thereby form a longer filter pathway. These teachings will also accommodate combining pleated sheets with unpleated sheets to form multiple stages of such material.

Figure 5:
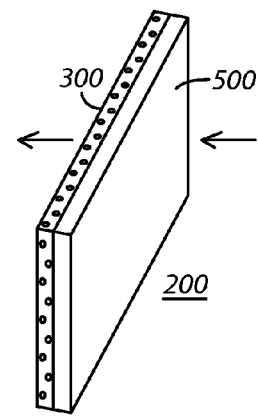
FIG. 5 comprises a perspective view as configured in accordance with various embodiments of the invention.

Or, and referring now to FIG. 5, the aforementioned filter material 300 can be combined with at least a second active layer of filter material 500 that is different than the first active layer of filter material 300. For example, by one approach, the second active layer of filter material 500 can offer a low pH environment (created, by way of example and at least in part, by the use of citric acid) that serves as a different modality of anti-microbial agent to thereby inactivate microbes using an alternative approach. By one approach, and as illustrated, the two layers of filter materials 300 and 500 can be juxtaposed immediately adjacent one another (and held in combination with one another using an adhesive or other attachment mechanism of choice if desired) with the second active layer of filter material 500 being disposed upstream of the first active layer of filter material 300.

Also if desired, this second active layer of filter material 500 can have a hydrophilic coating (such coatings being known in the art) on a spunbond fabric comprised of polypropylene to thereby attract water-borne microbes to the surfaces of one or both layers of filter material.

If desired, in combination with the above or in lieu thereof, other anti-microbial materials can serve in these same regards. As one illustrative example in these regards, the anti-microbial air filter can comprise a serpentine pneumatic pathway formed at least in part of Microban plastics (or the like) that include anti-bacterial additives to inactivate microbes on contact. So configured, and depending upon the length of the serpentine pneumatic pathway and the number and shape of the pathway contortions, at least many airborne microbes will contact a wall of the serpentine pathway while making the transit from an input to an output and become inactivated as a result of that contact.

Figure 6:
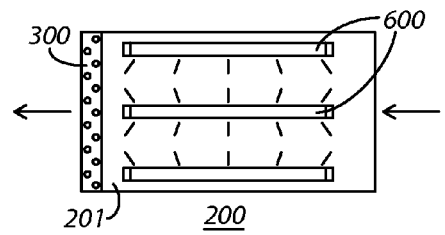
FIG. 6 comprises a side elevational sectioned schematic view as configured in accordance with various embodiments of the invention.

As another example in these regards, and referring now to FIG. 6, by one approach the anti-microbial air processor 200 can include (alone or in combination with other anti-microbial agents such as the aforementioned anti-microbial air filter) one or more ultraviolet light sources 600 that are again disposed with respect to an airway 201 of choice as corresponds to the personal patient warming apparatus to expose at least one inner surface of the personal patient warming apparatus to short-wave germicidal ultraviolet light (sometimes denoted in the art as UV-C) to thereby again inactivate microbes.

Figure 7:
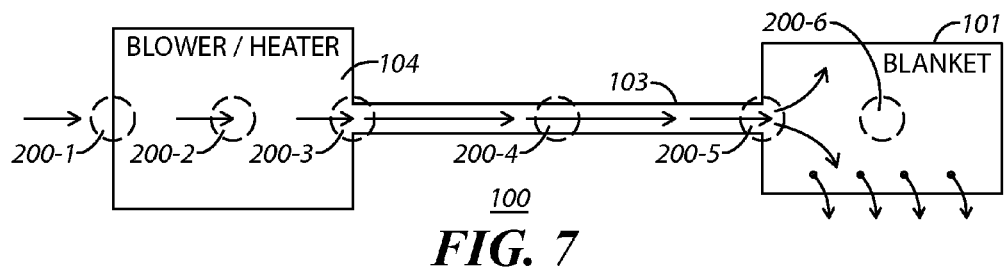
FIG. 7 comprises a side elevational schematic view as configured in accordance with various embodiments of the invention.

Generally speaking, and referring now to FIG. 7, the present teachings are highly flexible as regards the placement of the anti-microbial air processor 200 with respect to the portable patient warming apparatus 100. Examples include:

- at the air intake port of the heater/blower 104 (as denoted by reference numeral 200-1);
- internal to the heater/blower 104 (as denoted by reference numeral 200-2);
- at the air output port of the heater/blower 104 and/or at the input of the warm air delivery tube 103 (as denoted by reference numeral 200-3);
- within the warm air delivery tube 103 (as denoted by reference numeral 200-4);
- at the output of the warm air delivery tube 103 and/or at the input to the pneumatic blanket 101 (as denoted by reference numeral 200-5); and/or
- within the pneumatic blanket 101 (where, for example, all or part of the internal surfaces of the pneumatic blanket air chamber are faced with an anti-microbial material of choice) (as denoted by reference numeral 200-6).

When the anti-microbial air processor 200 comprises an anti-microbial air filter, the filter can be configured as a replaceable part or can be configured as an integral part of the corresponding component. For example, when the anti-microbial air filter is used in conjunction with the heater/blower 104 it can be useful, convenient, and economical to configure the anti-microbial air filter as a replaceable component. As another example, when the anti-microbial air filter is used in conjunction with the pneumatic blanket 101, it may be more appropriate to configure the filter as an integral part of the blanket 101 that is disposed of following a one-time use of the blanket 101.

Figure 8:
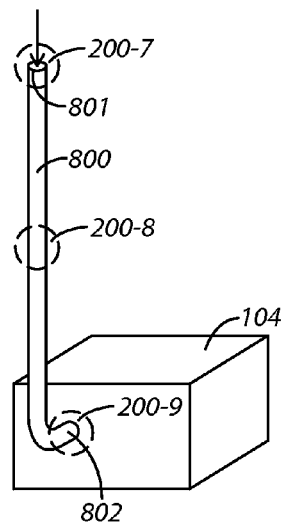
FIG. 8 comprises a perspective schematic view as configured in accordance with various embodiments of the invention.

By way of yet another example, and referring now to FIG. 8, these teachings will accommodate using a snorkel 800 having an air-intake port 801 that is disposed at least one meter above the heater/blower intake port and an air-output port 802 that is pneumatically coupled to the heater/blower intake port. The point of such an arrangement is to arrange for the heater/blower 104 to utilize air that is higher in the room and hence less contaminated (at least in many cases) than the air that is lower in the room. In such a case the anti-microbial air processor 200 can be located at the air intake port 801 of the snorkel 800 as denoted by reference numeral 200-7, somewhere along the length of the snorkel 800 as denoted by reference numeral 200-8, and/or at the air-output port 802 of the snorkel 800 as denoted by reference numeral 200-9.

So configured, warmed air that a personal patient warming apparatus delivers to a patient can be significantly cleansed of active microbes. That reduction in the number of active microbes, in turn, can help to avoid infections and other problems that might otherwise be experienced by the patient. In many cases these teachings can be implemented in cost-effective ways and can be maintained and used without significant training requirements.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. An apparatus comprising:
an anti-microbial air processor configured and arranged to fit at least substantially across an airway in a personal patient-warming apparatus to thereby inactive airborne microbes before those airborne microbes are exposed to a patient via warming air delivered by the personal patient-warming apparatus wherein the anti-microbial air processor is disposed in
a pneumatic warming blanket that comprises a part of the personal patient-warming apparatus.

2. The apparatus of claim 1 wherein the anti-microbial air processor comprises, at least in part, an anti-microbial air filter.

3. The apparatus of claim 2 wherein the anti-microbial air filter includes at least one active layer of filter material.

4. The apparatus of claim 3 wherein the active layer of filter material includes positively-charged ions that bind with negatively-charged groups present on at least some microbes to thereby inactivate the microbes.

5. The apparatus of claim 4 wherein the positively-charged ions include at least one of copper ions, zinc ions, and silver ions.

6. The apparatus of claim 5 wherein the positively-charged ions include both of copper ions and zinc ions.

7. The apparatus of claim 6 wherein the copper and zinc ions are disposed within a fabric substrate.

8. The apparatus of claim 7 wherein the fabric substrate is pleated to form a longer filter pathway.

9. The apparatus of claim 3 wherein the anti-microbial air filter includes at least a second active layer of filter material.

10. The apparatus of claim 9 wherein the second active layer of filter material has a hydrophilic coating.

11. The apparatus of claim 10 wherein the second active layer of filter material has a low pH environment to thereby inactivate microbes.

12. The apparatus of claim 11 wherein the low pH environment is created, at least in part, by citric acid.

13. The apparatus of claim 9 wherein the second active layer of filter material is disposed upstream of the first active layer of filter material.

14. The apparatus of claim 1 wherein the anti-microbial air processor further includes a component that is disposed at an intake for a blower.

15. The apparatus of claim 1 wherein the anti-microbial air processor further includes a component that is disposed at an output port for a blower.

16. The apparatus of claim 1 wherein the anti-microbial air processor comprises, at least in part, an ultraviolet light source configured to expose at least one inner surface of the personal patient-warming apparatus to ultraviolet light to thereby inactive microbes.

17. The apparatus of claim 1 further comprising:
an air-intake snorkel having an air-intake port disposed at least one meter above a blower intake for the personal patient-warming apparatus and an air-output port pneumatically coupled to a blower intake.

* * * * *